(12) United States Patent
O'Brien et al.

(10) Patent No.: US 7,339,088 B1
(45) Date of Patent: Mar. 4, 2008

(54) ALKYLBENZENE REFINING PROCESS AND APPARATUS

(75) Inventors: Dennis E. O'Brien, Arlington Heights, IL (US); Douglas G. Stewart, Wheeling, IL (US); Bipin V. Vora, Naperville, IL (US)

(73) Assignee: UOP LLC, Des Plaines, IL (US)

( * ) Notice: Subject to any disclaimer, the term of this patent is extended or adjusted under 35 U.S.C. 154(b) by 503 days.

(21) Appl. No.: 10/974,271

(22) Filed: Oct. 27, 2004

(51) Int. Cl.
*C07C 7/04* (2006.01)
*B01D 3/00* (2006.01)

(52) U.S. Cl. .................. 585/804; 203/74; 203/75; 203/78; 203/81; 203/82; 202/158; 202/161

(58) Field of Classification Search .......... 196/211; 202/158; 203/69, 75, 78, 82, 84, 98; 585/319, 585/323, 800, 802, 804, 805, 807
See application file for complete search history.

(56) References Cited

U.S. PATENT DOCUMENTS

| 4,423,278 | A | 12/1983 | Yang et al. ............... 585/823 |
| 4,433,196 | A | 2/1984 | Yang et al. ............... 585/823 |
| 4,468,476 | A | 8/1984 | Yang et al. ............... 502/83 |
| 4,795,550 | A | 1/1989 | Sachtler et al. .......... 208/307 |
| 6,031,144 | A | 2/2000 | Campbell et al. ......... 585/449 |

OTHER PUBLICATIONS

Pujado, Peter R.; "Linear Alkylbenzene (LAB) Manufacture"; *Handbook of Petroleum Refining Processes* Edited by: Robert A. Meyers (New York, McGraw-Hill, 2nd Edition 1996) pp. 1.53-1.66 ISBN 0-07-041796-2 TP690.H34.

*Primary Examiner*—Glenn A. Caldarola
*Assistant Examiner*—Randy Boyer
(74) *Attorney, Agent, or Firm*—Arthur E. Gooding

(57) ABSTRACT

Improved processes and apparatus use a finishing column with a mid-cut that provides alkylbenzene products of high purity containing less than about 1 ppmw benzene and less than about 50 ppmw heavies while accommodating enhancements in the efficiencies and the capacities of the distillation train to recover alkylbenzene from alkylation reaction product and while enabling the use of catalytic treatments to reduce olefinic-component content.

20 Claims, 5 Drawing Sheets

ALKYLBENZENE REFINING PROCESS AND APPARATUS

FIELD OF THE INVENTION

This invention pertains to improvements in refining alkylbenzene streams, especially streams produced by the alkylation of benzene, by distillation to provide at least one of enhanced product quality and increased production capacity.

BACKGROUND OF THE INVENTION

The alkylation of benzene with acyclic olefins is a widely practiced commercial process. Alkylbenzenes are produced as a commodity product in large-scale facilities, e.g. often in amounts of 50,000 to 200,000 metric tons per year per plant. The alkylbenzenes find a variety of applications, the most prevalent of which is to be converted into detergents by sulfonation and neutralization. The alkylbenzene must meet stringent product specifications to be commercially acceptable. The benzene content of the product should be relatively free from benzenes, e.g., less than about 1 part per million by weight (ppmw), and often less than about 0.5 ppmw. Also, desirable alkylbenzene products are relatively free, e.g., less than about 50, preferably less than about 5, ppmw, from byproducts such as dialkylbenzenes, oligomers of olefins, and the like (herein referred to as "heavies"). The heavies content of a stream can be determined by ASTM D-2887-04a, Standard Test Method for Boiling Range Distribution of Petroleum Fractions by Gas Chromatography, which is in effect on Jul. 31, 2004, available from ASTM International, West Conshohocken, Pa., United States of America.

Another purity issue associated with alkylbenzenes is the absence of color formers, or color bodies. Color bodies are components that impart color to the alkylbenzene. Saybolt color is one procedure for determining color of a liquid and for purposes herein refers to ASTM D-156-00, Standard Test Method for Saybolt Color of Petroleum Products (Saybolt Chronometer Method), which is in effect on Jul. 31, 2004, available from ASTM International. Desirable alkylbenzenes have a Saybolt color of at least +25, and preferably at least +29.

Often a bromine index is used to evaluate the quality of an alkylbenzene product. Although the bromine index relates primarily to olefin content, generally a correlation exists between the bromine index and the color of the alkylbenzene and of sulfonated alkylbenzenes made therefrom, e.g., as determined by the Klett color index. Typically, the bromine index of an alkylbenzene should be less than about 20, preferably less than about 5. There are a number of methods for determining a bromine index of an alkylbenzene, but the methods often provide results that are not consistent with each other. Hence, for purposes herein, the bromine index is that measured by UOP Method 304-90, "Bromine Number and Bromine Index of Hydrocarbons by Potentiometric Titration", which is in effect on Jul. 31, 2004, available from ASTM International.

Typically, alkylbenzene is purified by the use of several distillation steps. For instance, see Pujado, *Linear Alkylbenzene (LAB) Manufacture*, in Handbook of Petroleum Refining Processes, by Robert A. Meyers, Second Edition, pp 1.53 to 1.66, McGraw-Hill, New York (1996), especially pages 1.56 to 1.60. In general, the alkylation reaction product is subjected to a first distillation in a benzene column to separate benzene as an overhead stream that can be recycled to the alkylation reaction. The bottoms stream from the benzene column is then subjected to a distillation to separate paraffins and unreacted olefin in a paraffins column. The paraffins-containing overhead is capable of being recycled to a paraffin dehydrogenation unit while the bottoms stream is passed to a heavy alkylate distillation column. In the heavy alkylate distillation column, heavies are separated from the lighter alkylbenzene, and a heavies-containing stream is withdrawn as a bottoms stream. If desired, the bottoms stream can be subjected to a further distillation to recover additional alkylbenzene.

Several modifications to this refining scheme have been proposed. For instance, in U.S. Pat. Nos. 4,423,278; 4,433,196 and 4,468,476, the use of clay treatment has been proposed to reduce color formers in the product. U.S. Pat. Nos. 4,795,550 and 6,031,144 disclose the use of acidic catalysts to reduce olefin content.

The stream to be acid treated could, for instance, be the feed to the heavy alkylate distillation column. Thus, the heavy alkylate distillation column could be used to remove heavies produced by the acidic catalyst. However, the amount of olefin-containing components contained in the feed stream is such that catalyst replacement or regeneration must be very frequent or very large volume catalyst beds must be used. Accordingly, where acid treatment has been used, it has been to treat the overhead from the heavy alkylate distillation column.

In one commercially practiced process, the alkylbenzene from the heavy alkylate distillation column is subjected to clay treatment and then is passed to a finishing distillation column. A benzene-containing overhead stream is withdrawn, and the desired alkylbenzene is recovered as the bottoms stream. This variation has the benefit of removing any benzene contained therein. Benzene, for instance, may be coproduced during the clay treatment, e.g., by transalkylation of the alkylbenzene to dialkylbenzene and benzene, or may result from degradation of the alkylbenzene during upstream distillation operations.

A number of factors arise in designing a distillation system for recovering alkylbenzene from the alkylation of benzene. One consideration is that components contained in the alkylation product, including the alkylbenzene, can undergo further reaction or degradation. For this reason, the temperatures in the distillation processes are maintained sufficiently low that undue reaction or degradation does not occur, usually below about 300° C., preferably below about 270° C. Thus, at least the heavy alkylate distillation column is operated at subatmospheric pressure, e.g., from about 0.5 to 10, often about 1 to 3, kPa absolute. Not only does operation at subatmospheric pressure entail energy expense to maintain the sought vacuum, but also the ability to increase the volume of alkylation product processed is impaired due to practical temperature limitations as well as the vacuum capacity. Additionally, it is generally desired to minimize the residence time of the alkylation product in the column at higher temperatures. Hence, lower reflux ratios are often preferred. These lower reflux ratios provide a risk that an excursion from the desired conditions in the column may occur and an instability would result. A further implication is that to maintain a desired overhead purity, that is, with little heavies in the alkylbenzene-rich overhead, the bottoms may contain significant amounts of the desired alkylbenzene product.

Other considerations, especially for commercial facilities, are energy and equipment integration and capital costs. A primary consideration for energy consumption of a refining system is the heat required for the reboilers for each of the distillation columns. A significant factor determining the reboiler heat, or duty, is the amount of reflux required to achieve the sought degree of separation, i.e., reflux ratio (R/F), which is the mole ratio of reflux to feed to the column. Thus, to maintain a given degree of separation, as the flow rate of feed is increased, the reboiler heat required must also be increased to enable the reflux ratio to be maintained.

Significant financial benefit can be achieved through even slight improvements in efficiency or reductions in energy consumption or increases in capacity in a given existing plant, e.g., through debottlenecking. Unfortunately, the demands placed upon alkylbenzene product quality give little room for debottlenecking the distillation train while maintaining advantageous operating costs.

Accordingly, processes are sought by which the product quality of the alkylbenzene product can be maintained or improved while increasing the capacity of a given distillation train for purifying alkylbenzene. Processes are also sought to reduce energy consumption for purification per unit of alkylbenzene product. Processes are additionally sought to obtain alkylbenzene having desirable absence of benzene and heavies where the catalytic treatment to remove olefins is subsequent to the separation of heavies.

SUMMARY OF INVENTION

By the present invention processes and apparatus are provided that facilitate obtaining alkylbenzene products of high purity, e.g., containing less than about 1 ppmw benzene and less than about 50 ppmw heavies, while accommodating enhancements in the efficiencies and the capacities of the distillation system to recover alkylbenzene from alkylation reaction product and while enabling the use of catalytic treatments to reduce olefinic-component content. In accordance with this invention, an alkylbenzene-containing stream from the overhead from a heavy alkylate distillation is subjected to a further fractionation by distillation to provide an overhead containing lights ("lights" being components having a normal boiling point less than the alkylbenzene such as benzene and alkane), a bottoms stream containing heavies and alkylbenzene product as a mid-cut.

In additional detail, the broad aspects of the processes of this invention for refining an alkylbenzene stream, which stream comprises alkylbenzene of 15 to 25 carbon atoms, alkane, benzene and heavies, comprise:

a. separating by distillation at least about 99.5, preferably at least about 99.9, percent of the benzene contained in said stream to provide a first overhead comprising benzene and a first bottoms stream comprising alkylbenzene, alkane and heavies;

b. separating by distillation at least about 90, preferably at least about 95, weight percent of the alkane contained in said first bottoms stream to provide a second overhead comprising alkane and a second bottoms stream comprising alkylbenzene and heavies;

c. separating by distillation at least about 60, preferably at least about 80, weight percent of the heavies contained in the second bottoms stream to provide a third bottoms stream comprising heavies and a third overhead comprising alkylbenzene and heavies, said third overhead preferably containing at least about 0.5, and often about 1 to 10, weight percent heavies; and d. separating by distillation alkylbenzene a fourth distillation composition comprising the third overhead, said distillation providing a fourth overhead comprising alkylbenzene, preferably at least about 40 mole percent alkylbenzene, and lights; a fourth bottoms stream comprising alkylbenzene, preferably at least about 80 mole percent alkylbenzene, and heavies; and a mid-cut containing alkylbenzene and less than about 1 ppm by weight benzene and less than about 50 ppm by weight heavies, and preferably the mid-cut has a bromine index of less than about 5.

Thus, the processes of this aspect of the invention, by providing for an additional fractional distillation to remove both lights and heavies, do not require the other distillations to effect the sought removal of lights and heavies. Therefore, the capacity of these distillations can increase or the reflux ratios can decrease for these distillations. Lower reflux ratios provide for reduced energy consumption.

In an advantageous embodiment of this aspect of the invention, the third distillation, which is a heavy alkylate distillation, can be operated such that the bottoms stream contains less than about 15, preferably less than about 10, mole percent alkylbenzene. With such a low concentration in the bottoms stream, which bottoms stream is typically small, an economically attractive process may not require the use of an alkylbenzene recovery column to capture alkylbenzene that would otherwise be lost with the heavies. The third distillation can be operated to result in a greater concentration of heavies in the overhead as the fourth distillation serves to provide desirable alkylbenzene product quality, e.g., with less than about 50 ppm by weight heavies and often less than about 30 ppm by weight heavies. Frequently, the reflux ratio for the third distillation is less than about 0.7, say about 0.2 to 0.65. Thus benefits can be achieved in capacity, energy consumption as well as stability.

The distillation of step (d) need not be operated to maximize the recovery of alkylbenzene contained in the fourth overhead. In fact benefits flow from the processes of this invention even where the concentration of alkylbenzene in each of the fourth overhead and the fourth bottoms stream is significant. In preferred aspects of the processes of this invention, the fourth distillation serves to reduce reboiler energy demand for at least one of the second and third distillations and/or to increase capacity of at least one of the second and third distillations. Accordingly the relative amount of the fourth overhead stream and the fourth bottoms stream, and the concentration of alkylbenzene in such streams, will be related to the operation of the second and third distillations. Usually the concentration of alkylbenzene in the fourth overhead stream is at least about 40 mole percent and may even be greater than 99 mole percent. Typically the concentration of alkylbenzene in the fourth bottoms stream is greater than about 60, say, at least about 80, mole percent and can be greater than 99 mole percent. The flow rates of the fourth overhead stream and the fourth bottoms stream are a fraction of that of the mid-cut. For instance the flow rate of each of the fourth overhead stream and the fourth bottoms stream is less than about 20, preferably less than about 10, mole percent of the feed to the fourth distillation.

In preferred aspects of the invention, at least a portion of the overhead and the bottoms stream of the distillation of step (d) are recycled to recover the contained alkylbenzene. For instance, the lights-containing fourth overhead is passed to the distillation of step (a) where benzene, paraffin and any alkylbenzene contained in the overhead can be recovered or to the distillation of step (b) where paraffin and any alkylbenzene contained in the overhead can be recovered. At least a portion of the bottoms stream can be passed to the distillation of step (c) for recovery of the alkylbenzene. Thus, the distillation of step (d) need not entail a large number of theoretical separation plates or significant energy consumption by the reboiler which would be required for achieving higher reflux ratios and thus more complete separations.

In a preferred aspect of the processes of the invention, the fourth distillation composition comprises an acid-treated stream generated from subjecting a stream comprising alkylbenzene to olefin reduction conditions including the presence of an acidic catalyst. The acid-treated stream may, for instance, be a side draw from the fourth distillation that is treated and returned to the distillation or, preferably, is the overhead of the third distillation that has been subjected to olefin reduction conditions. The additional distillation of this invention removes benzene and heavies that may result from the olefin reduction operation. Often, the bromine index of the alkylbenzene product that has been treated in such an olefin reduction step is less than about 5, preferably less than about 1.

Another broad aspect of the processes of this invention comprises:
a. contacting a stream comprising alkylbenzene of 15 to 25 carbon atoms and olefinic-components with an acidic solid under olefin reduction conditions to reduce the concentration of olefinic-components whereby benzene and heavies are produced, and an acid-treated stream is provided, and
b. separating by distillation alkylbenzene from the acid-treated stream, said distillation providing an overhead comprising alkylbenzene and benzene, a bottoms stream comprising alkylbenzene and heavies, and a mid-cut containing alkylbenzene and less than about 1 ppm by weight benzene and less than about 50 ppm by weight heavies, and the mid-cut has a bromine index of less than about 5.

In the broad aspects of the apparatus of this invention, an alkylbenzene refining system is provided which comprises:
a. a benzene distillation assembly comprising an inlet adapted to receive an alkylbenzene-containing feed, an overhead outlet adapted to discharge a benzene-containing overhead stream, and a bottoms outlet adapted to discharge an alkylbenzene-containing stream;
b a paraffins distillation assembly comprising an inlet in fluid communication with the bottoms outlet of the benzene distillation assembly, an overhead outlet adapted to discharge an alkane-containing overhead stream, and a bottoms outlet adapted to discharge an alkylbenzene-containing stream;
c. a heavy alkylate distillation assembly comprising an inlet in fluid communication with the bottoms outlet of the paraffins distillation assembly, an overhead outlet adapted to discharge an alkylbenzene-containing overhead stream, and a bottoms outlet adapted to discharge a heavies-containing stream; and
d. a finishing distillation assembly comprising an inlet in fluid communication with the overhead outlet of the heavy alkylate distillation assembly, an overhead outlet adapted to discharge an alkylbenzene and lights-containing stream, a bottoms outlet adapted to discharge an alkylbenzene and heavies-containing stream, and a mid-cut outlet adapted to discharge an alkylbenzene-containing stream.

In the more preferred apparatus of the invention, the overhead outlet of the finishing distillation assembly is in fluid communication with the inlet to the benzene distillation assembly or the paraffins distillation assembly. In another more preferred apparatus of the invention, the bottoms outlet of the finishing distillation assembly is in fluid communication with the inlet to the heavy alkylate distillation assembly. In yet further preferred aspect of the apparatus of the invention, an olefin reduction catalytic converter is provided which comprises an inlet in fluid communication with the overhead outlet of the heavy alkylate distillation assembly and an outlet which is in fluid communication with the inlet to the finishing distillation assembly.

In another aspect of the apparatus of this invention, an alkylbenzene refining system comprises:
a. an olefin reduction catalytic converter comprising an inlet in adapted to receive an alkylbenzene-containing stream and an outlet adapted to discharge a treated, alkylbenzene-containing stream; and
b. a finishing distillation assembly comprising an inlet in fluid communication with the outlet of the catalytic converter, an overhead outlet adapted to discharge an alkylbenzene and benzene-containing stream, a bottoms outlet adapted to discharge an alkylbenzene and heavies-containing stream, and a mid-cut outlet adapted to discharge an alkylbenzene-containing stream.

The term "distillation assembly" as used herein contemplates the use of one or more distillation columns. Where more than one column is used in a distillation assembly, the columns may be parallel or at least a portion of any of the overhead, side-cut or bottoms stream of one column may be introduced into a subsequent column.

DETAILED DISCUSSION

Benzene Alkylation

Figure 1:
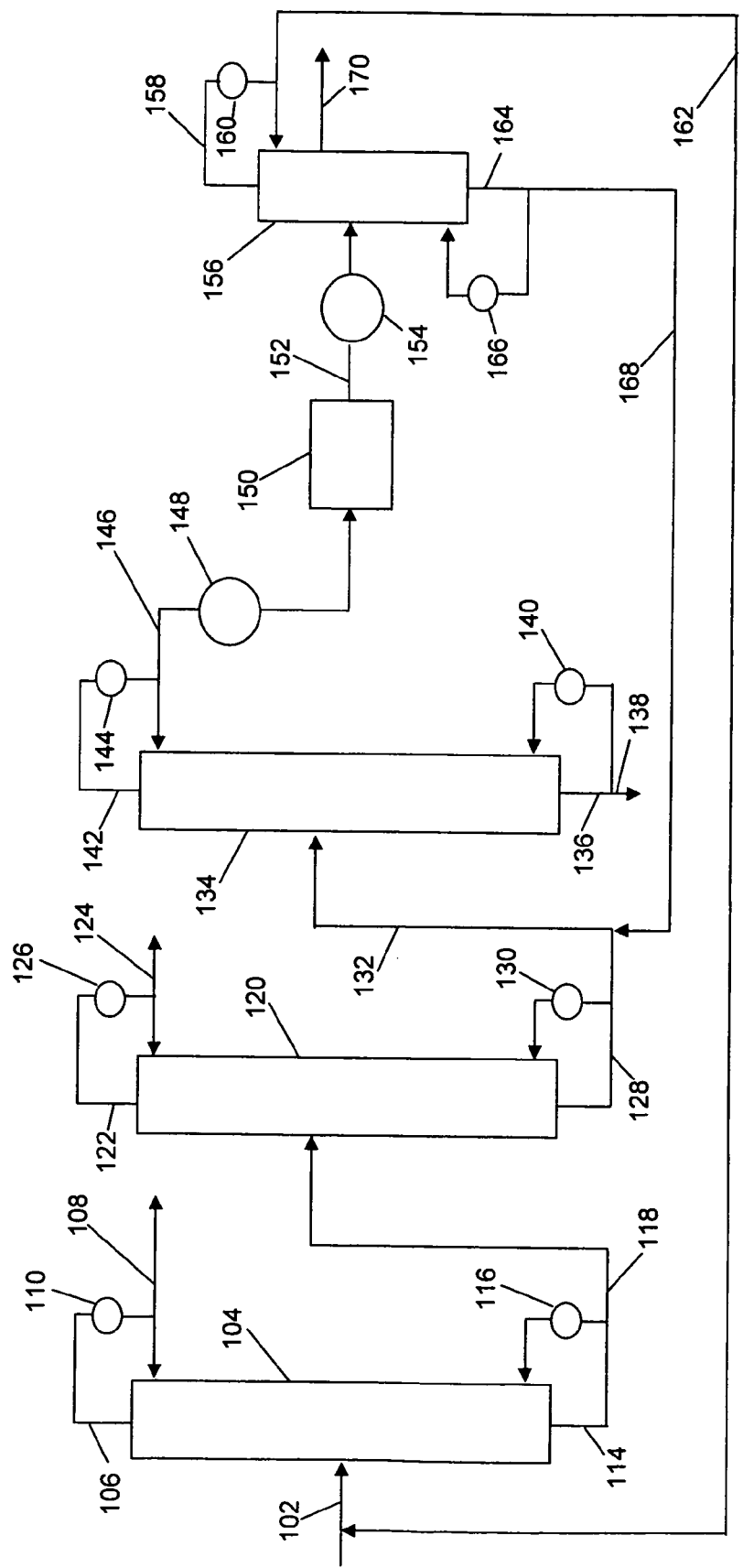
FIG. 1 is a schematic representation of an apparatus in accordance with this invention for refining alkylbenzene.

Various processes have been proposed for the alkylation of benzene. See, for instance, Pujado, *Linear Alkylbenzene (LAB) Manufacture*, Handbook of Petroleum Refining Processes, Second Edition, pp 1.53 to 1.66 (1996). The most common processes are those involving the presence of hydrogen fluoride ("HF Processes") and those involving the use of a solid acidic catalyst ("Solid Catalyst Processes"). In general, the HF Process and the Solid Catalyst Process involve contacting an olefin with a stoichiometric excess of benzene at elevated temperature to produce alkylbenzene. The reaction product stream will contain, in addition to alkylbenzene, benzene, some unreacted olefin, and reaction byproducts such as dialkylbenzene and oligomers and polymers of the olefin. For commercial processes, the feedstocks may include other components as well. For instance, the olefin may be obtained by the dehydrogenation of a paraffinic feedstock. See, for instance, U.S. Pat. No. 6,670,516, herein incorporated in its entirety by reference. Generally, for the olefin-containing portion of the feedstock, the feedstock comprises at least about 5.0 molar percent olefin.

The olefins used to make the alkylbenzenes used in the processes of this invention may vary widely and may be branched, linear or slightly branched acyclic olefins of from about 9 to 19, often 9 to 14, carbon atoms, and are often present in a feedstock as a mixture of olefins. Due to environmental concerns, where the alkylbenzenes are intended to be sulfonated to make detergents, the olefins are linear (making linear alkylbenzenes (LAB's) or slightly branched (making modified alkylbenzenes MAB's). The olefin-containing aliphatic compound is usually mono-olefinic. The positioning of the olefinic bond in the molecule is not critical as most alkylation catalysts have been found to promote migration of the olefinic bond. However, the branching of the hydrocarbon backbone is often more of a concern as the structural configuration of the alkyl group on the arylalkane product can affect performance. For instance, where arylalkanes are sulfonated to produce surfactants, undue branching can adversely affect the biodegradability of the surfactant. On the other hand, some branching may be desired such as the lightly branched modified alkylbenzenes such as described in U.S. Pat. No. 6,187,981, herein incorporated in its entirety by reference. The olefin may be unbranched or lightly branched, which as used herein, refers to an olefin having three or four primary carbon atoms and for which none of the remaining carbon atoms are quaternary carbon atoms. A primary carbon atom is a carbon atom which, although perhaps bonded also to other atoms besides carbon, is bonded to only one carbon atom. A quaternary carbon atom is a carbon atom that is bonded to four other carbon atoms. The olefin-containing aliphatic compound is usually a mixture of two or more olefins.

The amount of benzene present during the alkylation will depend upon the sought conversion selectivity to alkylbenzene. In general, the greater the stoichiometric excess of benzene, the greater the selectivity to alkylbenzene. Typically, the ratio of benzene to olefin during alkylation is within the range of about 5:1 to 50:1 or more. For the HF Processes, this ratio is often between about 5:1 to 10:1, and for the Solid Catalyst Processes, between about 10:1 to 30:1.

U.S. Pat. No. 4,463,205, herein incorporated by reference in its entirety, discloses typical HF Processes. In these HF Processes, the reactants are normally subjected to vigorous mixing and agitation at the point of initial contact of the olefin and the liquid-phase hydrogen fluoride. The alkylation zone preferably has an overall arrangement similar to that shown in U.S. Pat. No. 3,494,971. In this arrangement, the two feed hydrocarbons and liquid phase HF are charged to a reactor. The effluent of this reactor is passed into a first settling zone and separated into HF and hydrocarbon phases. The HF is withdrawn and divided into a portion passed into a regenerator and a portion returned to the reactor. A hydrocarbon phase is withdrawn from the first settling zone and charged to a contactor, which is sometimes referred to as a second "reactor", as the only hydrocarbon charged to the contactor. The HF charged to the contactor is a mixture of newly regenerated HF and HF withdrawn from a second settling zone, which receives the total effluent of the contactor. A portion of the HF withdrawn from the second settling zone is charged to the reactor to replace the HF withdrawn for regeneration. The hydrocarbon phase which is withdrawn from the second settling zone may be withdrawn as the alkylation zone effluent stream but is preferably passed into a stripping column in which dissolved HF is removed overhead and some of the feed aromatic hydrocarbon is also recovered. The net bottoms of this HF stripping column becomes the alkylation zone effluent stream charged to the fractionation zone of the subject process.

The alkylation reaction zone is maintained at alkylation-promoting conditions. As used herein, the term "alkylation-promoting conditions" is intended to include a pressure sufficient to maintain the reactants and HF in a liquid phase. A general range of operating pressures is from about 200 to 4500 kPa absolute. The temperature range covered by this set of conditions is from about −200 to about 95° C., but the reaction is preferably conducted at a temperature of from 15° to 70° C. The volumetric ratio of HF to the total amount of hydrocarbons entering the reactor should be maintained within the broad range of from about 0.2:1 to about 10:1, preferably from 0.5:1 to 2:1.

The effluent streams leaving the reactor will typically be an intimate admixture of liquid phase hydrocarbons and liquid phase hydrogen fluoride. They may be in the form of a true emulsion. A considerable residence time is normally required to separate these two liquid phases, and the effluent streams are therefore passed into settling zones. The two settling zones will normally be maintained at a temperature that is set by the entering HF-hydrocarbon mixtures withdrawn from the respective upstream zones. They will therefore be at substantially the same temperature as the immediately upstream reactor or contactor. The same is also normally true for the pressures used in the settling zones after adjustment for any pressure change due to liquid flow and elevation differences. The settling zones may however be downstream of control valves and therefore operated at a somewhat reduced pressure. This reduced pressure, however, must be superatmospheric and sufficient to maintain liquid phase conditions. A residence time for both the acid and hydrocarbon phases in the settling zones should be in excess of 30 seconds but less than 30 minutes.

Regeneration of the HF catalyst is normally accomplished by stripping the acid under conditions sufficient to decompose alkylfluorides and to produce an overhead vapor stream containing HF and the stripping media. Benzene available within the process is a suitable stripping media. The overhead vapor stream of the column is passed into a condenser, the resultant condensate is allowed to separate into an acid phase and a benzene phase containing dissolved HF.

The overhead vapor stream of the HF regeneration column will contain vapor-phase HF and the benzene. This vapor stream has a low concentration of the higher boiling impurities. The higher boiling materials are concentrated into a relatively small stream removed from the HF regeneration column as a net bottoms stream. The benzene present in the overhead vapor stream of the HF regeneration column is derived mainly from the reflux liquid fed to the top of this column. A small amount of benzene is also dissolved in the liquid phase HF stream fed to HF regeneration column. The reflux liquid is preferably removed from the overhead receiver, which collects the condensed overhead of the HF stripping column. It is not necessary to supply reflux liquid for successful operation of the HF regeneration column if the feed stream is passed into the top of the column.

The hydrocarbonaceous phase removed from the second settling zone is preferably passed into a stripping column referred to as the HF stripping column. The function of this column is to prevent the passage of HF into the downstream fractionation zone. Representative conditions for the operation of the HF stripping column include an overhead vapor temperature of about 1000 to 125° C. at a pressure of about 200 to 300 pKa gauge. There is normally no external reflux to this column. The overhead vapor stream of the HF stripping column is normally condensed by cooling it to about 35° C. or less.

In the Solid Catalyst Processes, benzene and the olefin are reacted under alkylation conditions in the presence of a solid alkylation catalyst. These alkylation conditions generally include a temperature in the range between about 80° C. and about 200° C., most usually at a temperature not exceeding about 175° C. Since the alkylation is typically conducted in at least partial liquid phase, and preferably in either an all-liquid phase or at supercritical conditions, pressures must be sufficient to maintain reactants in the desired phase. The requisite pressure necessarily depends upon the olefin and temperature, but normally is in the range of about 1300 to 7000 kPa(g), and most usually between about 2000 and 3500 kPa(g). Preferably the alkylation conditions do not result in substantial skeletal isomerization of the olefin. For instance, less than 15 mole percent, and preferably less than 10 mole percent, of the olefin, the aliphatic alkyl chain, and any reaction intermediate undergoes skeletal isomerization.

Alkylation of benzene by the olefins is conducted in a continuous manner, and one or more catalyst beds in flow series are used. For purposes herein, a catalyst bed is termed a reactor whether in the same or a separate vessel from another bed. In preferred processes of this invention 2 or 3 reactors can be used to achieve an advantageous combination of performance and capital expense avoidance.

The catalyst may be used as a packed bed or a fluidized bed. The feed to the reaction zone may be passed either upflow or downflow, or even horizontally as in a radial bed reactor. In one desirable variant, olefin-containing feedstock may be fed into several discrete points within the reaction zone, and at each zone the benzene to olefin molar ratio may be greater than 50:1. The total feed mixture, that is, aromatic compound plus olefin, is often passed through the packed bed at a liquid hourly space velocity (LHSV) between about 0.3 and about 6 $hr^{-1}$ depending upon, e.g., alkylation temperature and the activity of the catalyst. Lower values of LHSV within this range are preferred.

Any suitable alkylation catalyst may be used in the present invention, provided that the requirements for conversion, selectivity, and activity are met. Preferred alkylation catalysts comprise silica-alumina, fluorided silica-alumina, and zeolites having a zeolite structure type selected from the group consisting of BEA, MOR, MTW, and NES. Such zeolites include mordenite, ZSM4, ZSM-12, ZSM-20, offretite, gmelinite, beta, NU-87, and gottardite. Further discussion of alkylation catalysts can be found in U.S. Pat. Nos. 6,315,964 and 6,617,481.

The alkylbenzene stream useful in the processes of this invention may be from an alkylation process, including but not limited to, the HF Processes and the Solid Catalyst Processes described above, or may be from another source. In the aspects where the alkylbenzene stream is the effluent from an alkylation reactor, the stream generally has the components and concentrations as set forth in Table 1.

TABLE 1

| Component | Concentration (weight) | Typical Concentration (weight) |
| --- | --- | --- |
| Alkylbenzene | 0.05 to 30% | 2 to 25% |
| Benzene | 33 to 99% | 40 to 75% |
| Total olefin | 0.00001 to 2% | 0.0001 to 1% |
| Total paraffin | 0 to 25% | 1 to 20% |
| Heavies | 0.001 to 10% | 0.5 to 2% |

In the aspects of this invention involving the treatment of an alkylbenzene stream to reduce bromine index via a catalytic olefin reduction operation, the stream may vary widely in its composition. Usually the stream will contain at least about 90, preferably at least about 98, weight percent alkylbenzene, and may be substantially pure alkylbenzene containing only trace amounts of olefinic component, e.g., less than about 50 ppmw olefinic component.

Refining System

In the processes of this invention involving the use of a benzene distillation, a paraffin distillation and a heavy alkylate distillation, the benzene distillation is generally conducted with a bottoms temperature of less than about 300° C., preferably less than about 275° C., usually between about 230° and 270° C., and at a pressure at which the overhead is provided of between about 5 and 300, preferably between about 35 and 70, kPa gauge. The overhead generally contains less than about 2, preferably less than about 1.5, weight percent paraffins. The benzene distillation assembly may comprise one or more distillation columns. More than one overhead may be obtained from the benzene distillation assembly. For instance, a highly pure stream may be obtained for process needs such as regenerating catalysts or sorbents, e.g., having a paraffin concentration less than about 1, preferably less than about 0.1, weight percent. A lesser purity overhead may be obtained from the benzene distillation assembly, e.g., as a side draw, for use as a recycle to the alkylation reaction.

Each column may contain any convenient packing or distillation trays, but most often trays such as sieve and bubble trays, are used. Often the assembly provides at least about 5, say 6 to 70, and preferably 20 to 50, theoretical plates. The reflux ratio (herein defined as the distillate to reflux weight ratio) is often in the range of about 2:1 to 1:10, preferably about 1.5:1 to 1:5. The bottoms stream from the benzene distillation generally contains less than about 1000 ppmw, preferably less than about 50 ppmw, and sometimes less than about 5 ppmw, benzene. The benzene distillation may occur in a single column or two or more distinct columns may be used. For instance, a stripping column may be used to remove a portion, e.g., 20 to 50 percent, of the benzene and then the bottoms from the stripping column would be subjected to rectification in a subsequent column to obtain the desired separation.

The paraffin distillation is generally conducted with a bottoms temperature of less than about 300° C., preferably less than about 275° C., usually between about 250° C. and 275° C., and at a pressure at which overhead is provided of between about 5 and 110, preferably between about 10 and 50, kPa absolute. The column may contain any convenient packing or distillation trays, but most often sieve trays is used. Often the paraffins distillation assembly provides at least about 5, say 7 to 20, theoretical plates. The reflux ratio is often in the range of about 3:1 to 1:10, preferably about 1:1 to 1:3. The bottoms stream from the paraffins distillation generally contains less than about 10, preferably less than about 5, weight percent paraffins and preferably less than about 10, often less than about 1, ppmw benzene. Preferably, the bottoms stream contains between about 0.5 and 5, say about 1 to 5, weight percent paraffins. The paraffins distillation may occur in a single column or two or more distinct columns may be used.

As the processes of preferred aspects of the invention provide for a finishing distillation where a lights-containing overhead stream is provided, it is not essential that the paraffin distillation substantially remove all the paraffin from the alkylbenzene stream. Hence opportunities exist for energy savings. For instance, the amount of reboiler heat can be reduced as the internal reflux in the distillation column need not be as great as when the bottoms stream has a lesser concentration of paraffins. Also, for a given column, the capacity of the column can be increased, e.g., to debottleneck an existing refining system.

The heavy alkylate distillation is generally conducted with a bottoms temperature of less than about 300° C., preferably less than about 275° C., usually between about 250° C. and 275° C., and at a pressure of between about 0.5 and 30, preferably between about 1 and 5, kPa absolute. The column may contain any convenient packing or distillation trays, but most often structured packing is used. Often the heavy alkylate distillation assembly provides at least about 5, say 10 to 30, and preferably 10 to 20, theoretical plates. The reflux ratio is often in the range of about 2:1 to 1:5, preferably about 0.2:1 to 1:1. The overhead from the heavy alkylate distillation generally contains less than about 2 weight percent, preferably less than about 1 weight percent, and sometimes less than about 0.1 weight percent, total heavies. The benzene content of the overhead stream is generally less than about 5, preferably less than about 1, ppmw and the paraffins content is often less than about 10 weight percent.

Since the preferred aspects of this invention provide for a finishing distillation to remove, as a bottoms stream, heavies, the heavy alkylate column can be operated to permit significant amounts of heavies to be in the overhead. As with the paraffins distillation, the flexibility provided by these processes enables a reduction in reboiler duty for the heavy alkylate distillation. This reduction, in turn, reduces the reflux in the column thereby allowing more heavies to pass into the overhead stream. In addition to the reduction in reboiler heat duty that could be achieved, the capacity of a given distillation column can be increased.

The finishing distillation assembly serves to provide an alkylbenzene stream essentially free from benzene and heavies. In a preferred embodiment of the invention, the finishing distillation assembly can be operated to achieve the desired purity of the alkylbenzene in the mid-cut as opposed to maximizing the recovery of the alkylbenzene contained in the feed stream to the finishing distillation assembly. Thus, as discussed above, the overhead and the bottoms streams from the finishing distillation assembly can contain substantial amounts of alkylbenzene. For instance, the overhead may contain at least about 40 weight percent alkylbenzene and the bottoms stream may contain at least about 80 weight percent alkylbenzene. These streams can be returned to the benzene distillation assembly and the heavy alkylate distillation assembly, respectively, so that no net loss of alkylbenzene is suffered. By permitting the overhead and the bottoms stream to contain significant amounts of alkylbenzene, fewer theoretical plates are required thereby enhancing the economic attractiveness of using a finishing column and lower reflux ratios can be used resulting in energy savings.

The finishing distillation is generally conducted with a bottoms temperature of less than about 300° C., preferably less than about 275° C., usually between about 250° C. and 275° C., and at a pressure of between about 5 and 110, preferably between about 10 and 50, kPa absolute. The assembly may contain any convenient packing or distillation trays, but most often structured packing is used. Often the assembly provides at least about 2, say 5 to 20, theoretical plates. The mid-cut is generally taken from a point where at least 2, often at least 3, theoretical plates exist above and at least 2, often at least 3, theoretical plates exist below. Preferably the distillation assembly is a dividing wall column or has an internal column with a dedicated reboiler. The finishing distillation assembly may also be two separate columns.

The design and operation of the paraffins distillation assembly, the heavy alkylate distillation assembly and the finishing distillation assembly can vary widely within the broad aspects of the invention. This flexibility allows the designer or operator to achieve an objective for a particular situation. For instance, in debottlenecking an existing refining system, the paraffins distillation and/or the heavy alkylate distillation may be operated so as to increase capacity at the expense of a loss in separation. Alternatively, for a grass roots refining system, the paraffin distillation assembly and/or the heavy alkylate distillation assembly may be reduced in size, including a reduction in the number of theoretical distillation trays, to reduce capital costs. Also, reductions in reboiler heat duty for the paraffin distillation and/or the heavy alkylate distillation assembly may be the goal of the designer or operator. The reduction in such heat duties can be significant. By way of example, in preferred aspects of the invention, the reboiler energy consumption for the second and third distillations may be less than about 40, preferably less than about 25, kilocalories per kilogram of feed to the second distillation.

Acid Treatment

In the aspects of the processes of this invention where an alkylbenzene stream that contains olefinic components is subjected to a catalytic operation to improve bromine index, the alkylbenzene stream is passed to a catalytic conversion zone containing an acidic catalyst under olefin reduction conditions. The particular unit operation is not critical to the broad aspects of the invention and any suitable operation may be used.

A number of processes for improving the quality of alkylbenzenes and reducing olefin content have been proposed. The catalysts may be clay or molecular sieve (natural or synthetic). Included in the clays are montmorillonite, laponite, saponite, and pillared clays. Filtrol F-24 (Engelhard Corporation, Iselin, N.J.) is a preferred clay. Molecular sieves include zeolites A, beta, L, S, T, X and Y and omega, mordenite, erionite, chabazite, boggsite, cloverite, gmelinite, offretite, pentacil molecular sieves having silica to alumina ratios greater than about 10, and SAPO (such as SAPO 5 and 41). Engelhard Corporation represents that Filtrol F-24 has a pH of about 3.5.

The olefin reduction is typically conducted at temperatures between about 25° C. and 250° C., and most often between about 70° C. and 150° C., under a pressure sufficient to maintain the stream under liquid conditions, e.g., within the range of about 0.1 to 150 kPa absolute. The contact time with the catalyst is sufficient to provide the desired reduction in bromine index. For a fixed bed system, the weight hourly space velocity is typically in the range of about 0.1 to 20 $hr^{-1}$. The bromine index of the treated alkylbenzene stream is preferably below about 5, more preferably below about 2, and most preferably below about 1. The olefin reduction conditions also cause byproducts such as the formation of dialkylbenzene and benzene from alkylbenzene and form oligomers and polymers from olefinic components.

The effluent from the olefin reduction is subjected to the fourth distillation to remove as an overhead, benzene, and heavies such as the dialkylbenzene and the oligomers and polymers from olefinic components.

DESCRIPTION OF THE DRAWINGS

With reference to the drawings, FIG. 1 is a schematic representation of an apparatus in accordance with this invention which can be used to practice processes in accordance with this invention. An alkylbenzene stream, which may be a stream derived from the alkylation of benzene, is provided by line 102 to benzene column 104. Benzene column 104 is provided with overhead line 106 that receives gas phase overhead and directs it through condenser 110. A portion of the condensed overhead is passed to the top of column 104 as reflux. The remaining portion of the condensed overhead is withdrawn from line 106 via line 108. The benzene in line 108, for instance, may be returned to the alkylation reactor from which the alkylbenzene stream is obtained. Line 114 withdraws a bottoms stream from column 104 and directs a portion of the stream through reboiler 116 back to the bottom of column 104. Reboiler 116 may be heated in any suitable manner. Often hot oil or other heat transfer fluid is provided for the indirect heat exchange to vaporize the portion of the bottoms stream being returned to column 104.

The remaining portion of the bottoms stream is passed from line 114 to paraffins column 120 via line 118. Paraffins column is provided with overhead line 122 that receives gas phase overhead from the top of paraffins column 120. The overhead in line 122 is directed through condenser 126 and a portion is returned to paraffins column 120 as reflux. The other portion of the condensed overhead is withdrawn from line 122 and exits via line 124. If the alkylation process were integrated with a process for dehydrogenating paraffins to provide olefins for the alkylation, the overhead in line 124 would preferably be recycled to the dehydrogenation process. A bottoms stream from paraffins column 120 is withdrawn via line 128 and a portion is directed through reboiler 130 and reintroduced into the bottom of paraffins column 120. Reboiler 130 may also use hot oil or other thermal transfer fluid as the heat source. The remaining portion of the bottoms stream is passed from line 128 to heavy alkylate column 134 via line 132.

Heavy alkylate column 134 is provided with line 136 to withdraw a bottoms stream. A portion of the bottoms stream is reintroduced into the bottom of column 134 after being heated in reboiler 140. The remaining portion of the bottoms stream is withdrawn via line 138. The stream in line 138 usually contains some alkylbenzene. If desired, it can be directed to a recovery distillation column to recover additional amounts of alkylbenzene. Column 134 is also provided with overhead line 142 to withdraw a gaseous alkylbenzene-containing overhead stream. A portion of this stream is reintroduced into the top of column 134 after passing through condenser 144. The remaining portion of the alkylbenzene-containing overhead stream is passed via line 146 for catalytic olefin removal.

The stream in line 146 is passed through cooler 148 where it is cooled to a temperature suitable for catalytic olefin removal and then to catalytic olefin-removal reactor 150. An alkylbenzene stream containing a reduced amount of olefin component is withdrawn from reactor 150 and is passed via line 152 through heater 154 to finishing column 156. Heater 154 serves to increase the temperature of the stream to a desired temperature for distillation in finishing column 156. Finishing column 156 is provided with overhead line 158 that directs a benzene-containing overhead stream through condenser 160. A portion of the condensed overhead is returned to the top of finishing column 156 as reflux, and the remaining portion is passed via line 162 for combination with the alkylbenzene stream contained in line 102. A bottoms stream is withdrawn from finishing column 156 via line 164. A portion of the bottoms stream is vaporized in reboiler 166 and returned to the bottom of finishing column 156, and the remaining portion is directed via line 168 to line 132 where it is directed to heavy alkylate column 134. The alkylbenzene product is withdrawn via line 170.

Figure 2:
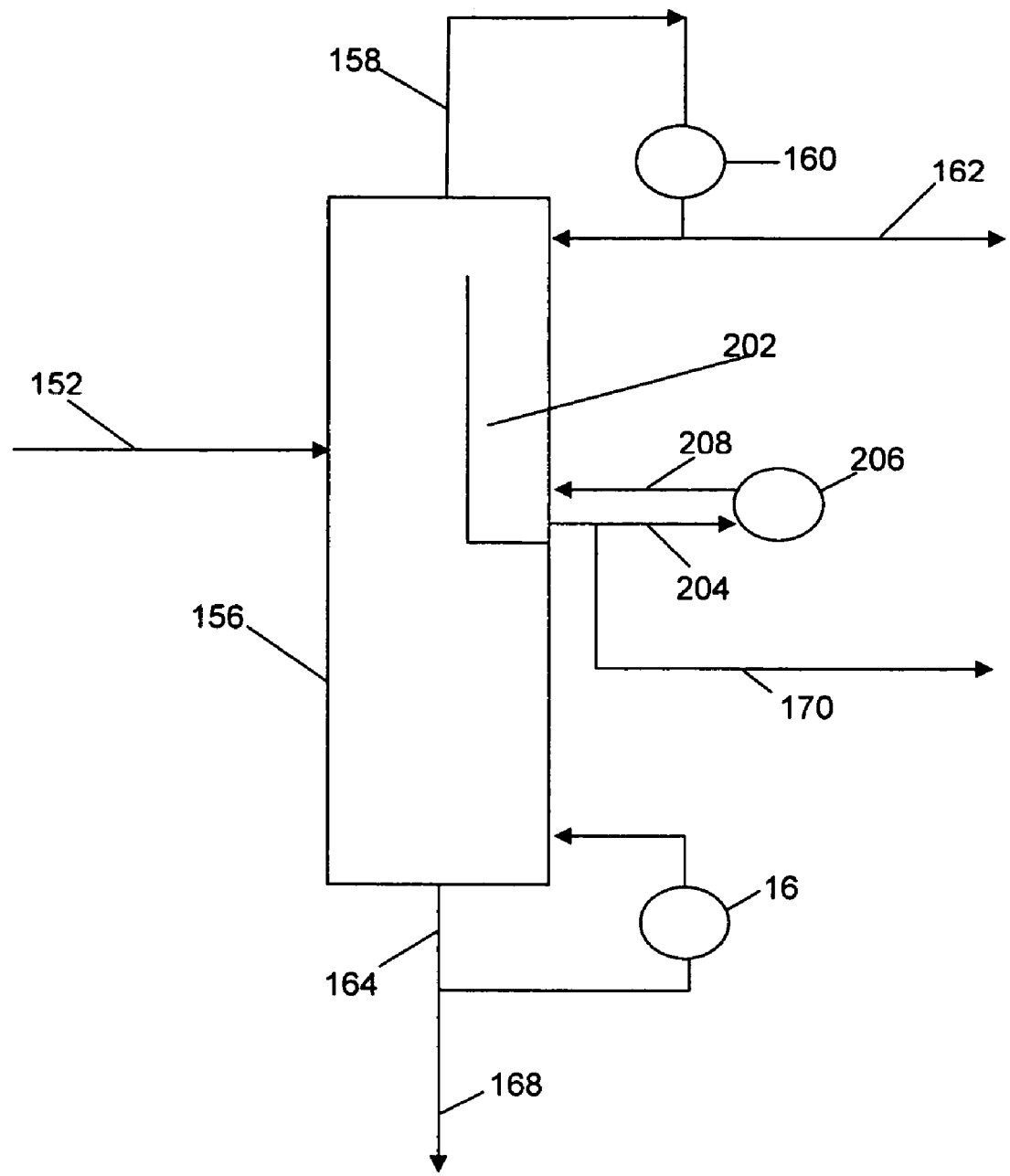
FIGS. 2, 3, 4 and 5 are schematic representations of various finishing distillation columns useful in the apparatus of this invention.

FIG. 2 is a schematic depiction of one type of finishing column that can be used in accordance with this invention. The numbers on FIG. 2 that are common with those on FIG. 1 refer to common features. As depicted, finishing column 156 is provided with fluid impermeable baffle 202 closing off an internal portion of the volume in the upper part of the column to define a distillation column internal to finishing column 156. Baffle 202 defines an opening at the top that will receive liquid phase from the top of the column and will allow vapors to flow into the overhead. Line 204 withdraws liquid at the bottom of the volume defined by the baffle and directs a portion to reboiler 206 for vaporization and a portion to line 170 as product alkylbenzene. The vapors generated in reboiler 206 are introduced into the bottom of the volume defined by baffle 202 via line 208. The internal column defined by baffle 202 serves to further reduce the benzene content of the alkylbenzene product.

Figure 3:
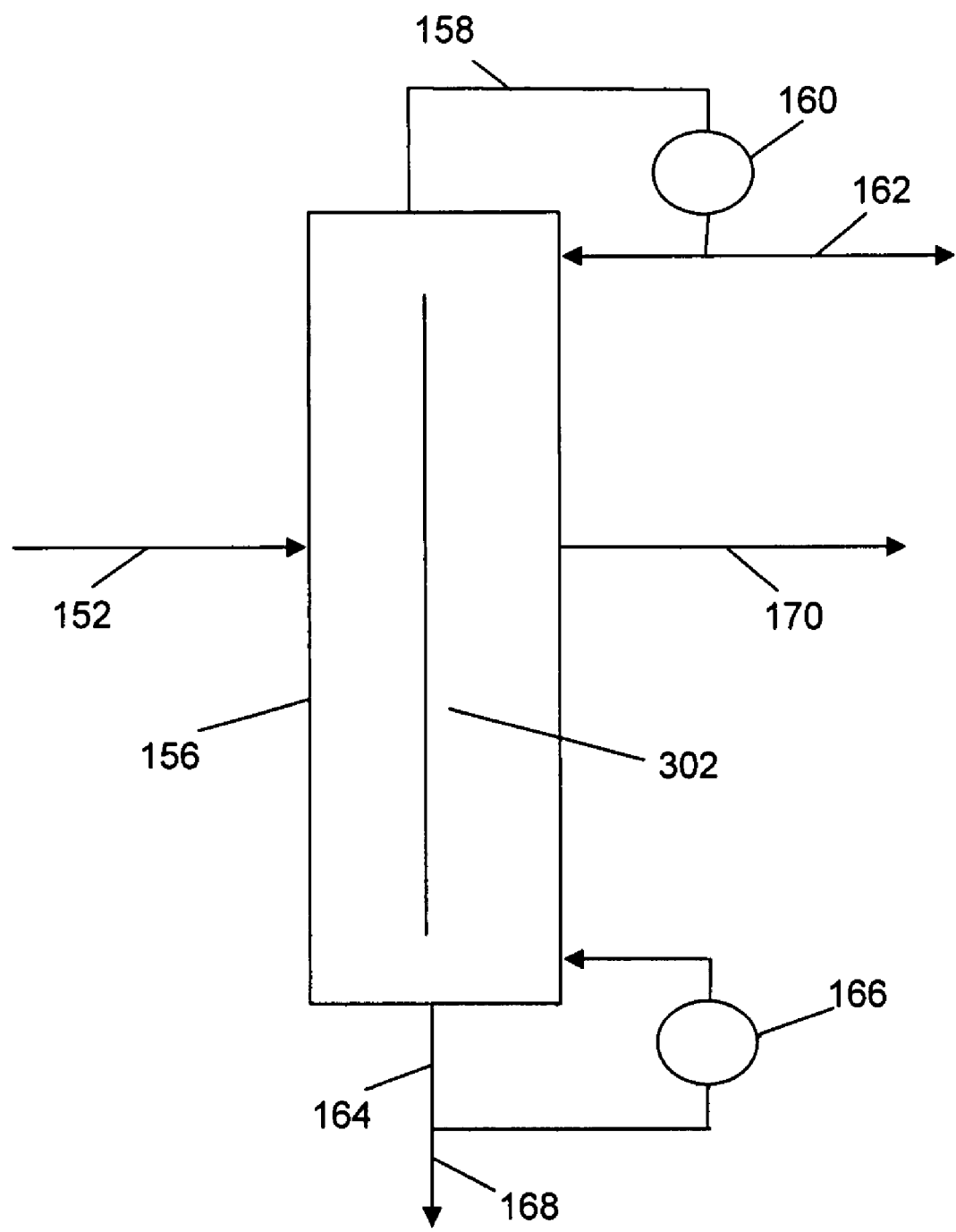

FIG. 3 is a schematic depiction of another type of finishing column that can be used in accordance with this invention. The numbers on FIG. 3 that are common with those on FIG. 1 refer to common features. As depicted, finishing column 156 is provided with fluid impermeable baffle 302 to provide a dividing wall column having a single reboiler. The alkylbenzene product is withdrawn via line 170 from the opposite side of baffle 302 from the introduction of the feed from line 152.

Figure 4:
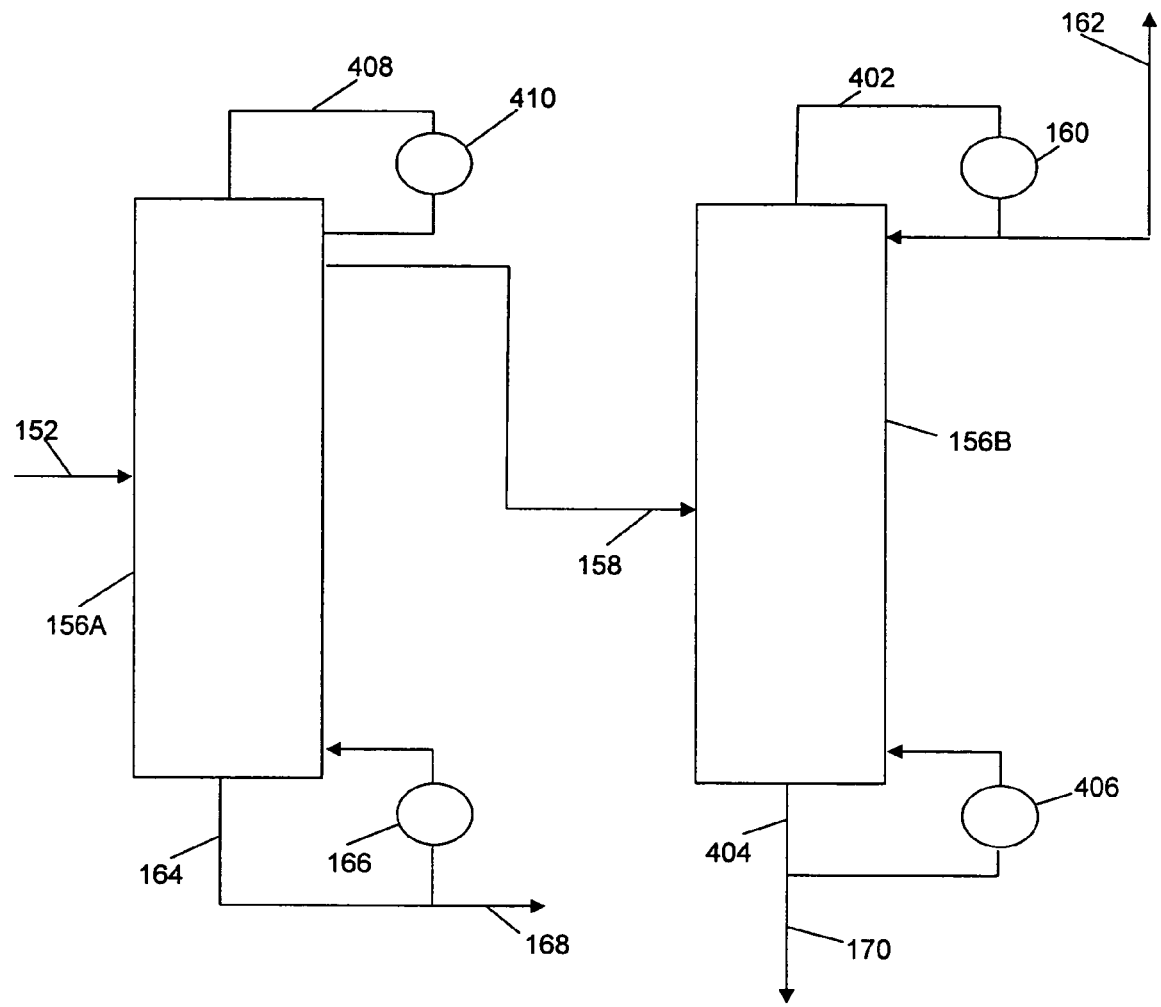

FIG. 4 is a schematic depiction of another type of finishing column comprising two distinct columns that can be used in accordance with this invention. The numbers on FIG. 4 that are common with those on FIG. 1 refer to common features. As depicted, the finishing column comprises heavies column 156A and product column 156B. Heavies column 156A is provided with line 408 having condenser 410 to withdraw an overhead stream, condense the stream and return it as reflux. A liquid phase stream is withdrawn from near the top of column 156A via line 158 and is introduced into product column 156B. The overhead from product column 156B is withdrawn via line 402 and condensed in condenser 160. A portion of this condensed overhead is introduced as reflux at the top of product column 156B. The remaining portion is withdrawn via line 162. A bottoms stream is withdrawn from column 156B via line 404. A portion of the bottoms stream is withdrawn via line 170 as product alkylbenzene and the remaining portion is passed through reboiler 406 and reintroduced into product column 156B.

Figure 5:
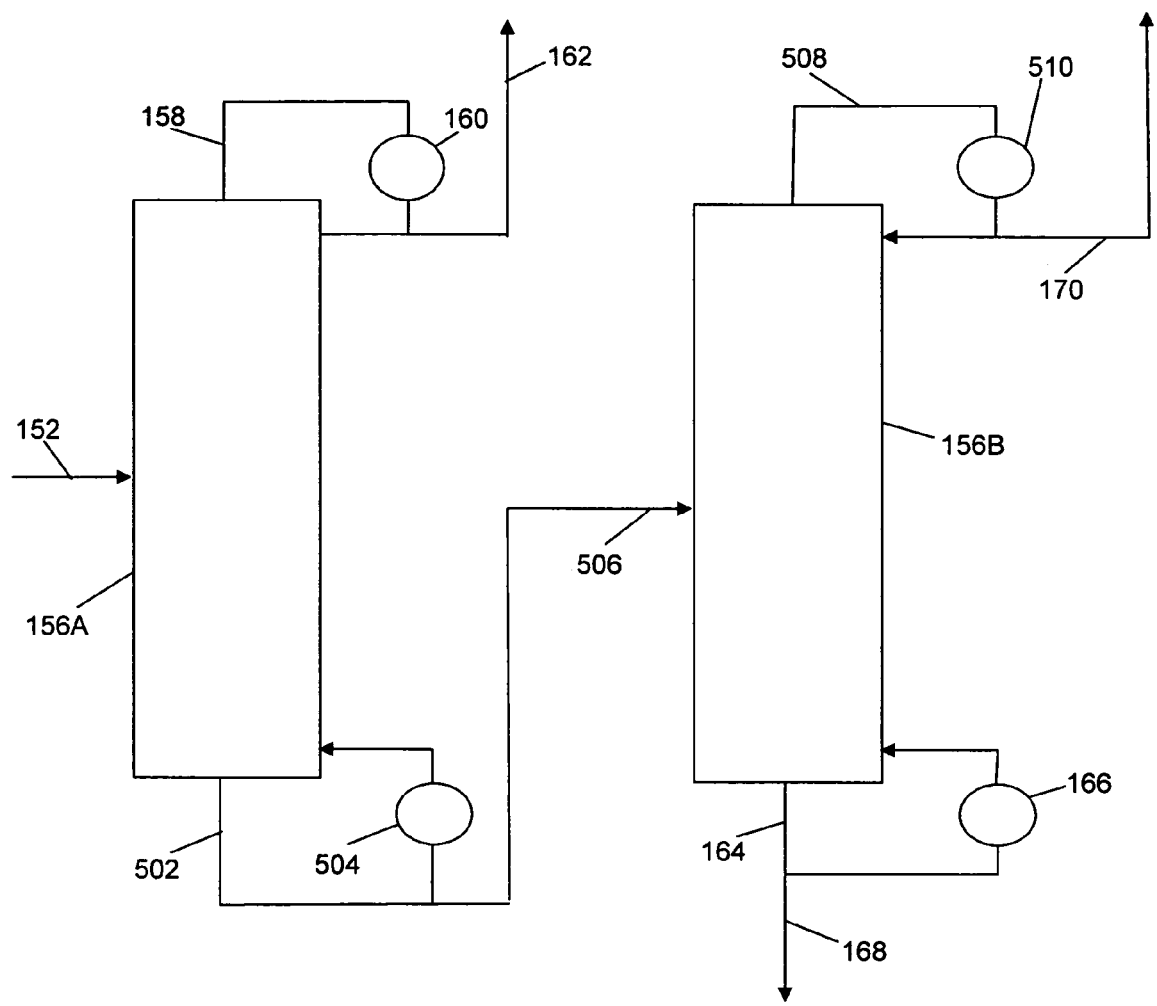

FIG. 5 depicts another two-column finishing distillation system. The numbers on FIG. 5 that are common with those on FIG. 1 refer to common features. As depicted, the finishing column comprises lights column 156A and product column 156B. A lights overhead is withdrawn from lights column 156A via line 158. Lights column is provided with line 502 to withdraw a bottoms stream. A portion of the bottoms stream is directed through reboiler 504 and is returned to the bottom potion of lights column 156A. The remaining portion of the bottoms stream is passed via line 506 to product column 156B. The overhead from product column 156B is withdrawn via line 508 and condensed in condenser 510. A portion of this condensed overhead is introduced as reflux at the top of product column 156B. The remaining portion is withdrawn as product alkylbenzene via line 170. A bottoms stream is withdrawn from column 156B via line 164. A portion of the bottoms stream is withdrawn via line 168 and the remaining portion is passed through reboiler 166 and reintroduced into the lower portion of product column 156B.

As stated above, the processes and apparatus of this invention can find application in debottlenecking the refining system of an existing alkylbenzene process. The increase in feed, however, will result in a decrease in the degree of separation and may run into problems such as insufficient reboiler capacity and instability of the gas-liquid contact in the column. Reflux ratios may be reduced to avoid reboiler capacity limitations, and increases in pressure may assist in enhancing stability. Either of these techniques will also result in a loss of selectivity of the separation. For instance, a loss of selectivity in the distillation in a paraffin distillation column such as depicted in FIG. 1 as column 120 will result in a greater concentration of paraffin in the bottoms stream 128. With respect to a heavy alkylate distillation column as depicted as column 134 in FIG. 1, the loss of selectivity can result in either a greater concentration of alkylbenzene in the bottoms stream 136 or a greater concentration of heavies in the overhead 142. The processes and apparatus of this invention enable a greater concentration of heavies in the overhead as they will be removed in finishing column 156. Thus the capacity increase can be obtained without undue loss of the desired alkylbenzene product.

The processes and apparatus of this invention also provide for energy savings in the paraffins distillation column and the heavy alkylate distillation column and can reduce the amount of alkylbenzene lost with the heavies in the bottoms stream discharge from the heavy alkylate distillation column. By way of illustration for a $C_{10}$ to $C_{13}$ olefin derived from a paraffin dehydrogenation process and benzene alkylation, the reflux ratio of a paraffins distillation column may be reduced from 0.8 to 0.6 and the pressure increased from about 13 to 19 kPa absolute resulting in a reduction in the reboiler duty of about 20 percent and a savings in vacuum costs with an increase in the vapor capacity of the column. The alkylbenzene concentration in the overhead would increase but still be under 0.01 mole percent, and the paraffin concentration in the bottoms would increase about 10 fold to about 5 mole percent. The reboiler duty of a heavy alkylate distillation column can also be reduced by about one third by reducing the reflux ratio from 1 to 0.5 and decreasing the bottoms pressure from about 4 to 2.6 kPa absolute. Under these conditions, the concentration of alkylbenzene in the bottoms stream would decrease by about a factor of 3 and the mole percent of heavies in the overhead would increase from about 0.003 to 0.023. Using the finishing column, the alkylbenzene product could still have less than about 0.02 mole percent paraffins and have a lesser heavies concentration.

When the overhead from the heavy alkylate distillation column is subjected to an olefin reduction operation, the benzene concentration would be present in parts per trillion and the heavies concentration would still be very low. If, for instance, the alkylbenzene were taken as the bottoms stream rather than a mid-cut as in the invention, the heavies would be contained in the alkylbenzene product. Where the overhead and the bottoms stream from the finishing column are recycled, the concentration of alkylbenzene is of little concern since it is not lost from the refining system. Accordingly, the finishing column can be operated with low recycle ratios to reduce reboiler duty.

It is claimed:

1. A process for refining an alkylbenzene stream, which stream comprises alkylbenzene of 15 to 25 carbon atoms, alkane, benzene and heavies comprising:
   a. separating by distillation at least about 99.5 percent of the benzene contained in said stream to provide a first overhead comprising benzene and a first bottoms stream comprising alkylbenzene, alkane and heavies,
   b. separating by distillation at least about 90 weight percent of the alkane contained in said first bottoms stream to provide a second overhead comprising alkane and a second bottoms stream comprising alkylbenzene and heavies and a reduced amount of alkane,
   c. separating by distillation at least about 60 weight percent of the heavies from the second bottoms stream to provide a third overhead comprising alkylbenzene and a third bottoms stream comprising heavies, and
   d. separating by distillation alkylbenzene from a fourth distillation composition comprising the third overhead, said distillation providing a fourth overhead comprising alkylbenzene and lights; a fourth bottoms stream comprising alkylbenzene and heavies; and a mid-cut containing alkylbenzene and less than about 1 ppm by weight benzene and less than about 50 ppm by weight heavies.

2. The process of claim 1 wherein the alkylbenzene from the mid-cut has a bromine index of less than about 5.

3. The process of claim 1 wherein at least a portion of the fourth overhead is passed to the distillation of step (a) or (b).

4. The process of claim 3 wherein at least a portion of the fourth bottoms stream is passed to the distillation of step (c).

5. The process of claim 1 wherein at least a portion of the fourth bottoms stream is passed to the distillation of step (c).

6. The process of claim 2 wherein the fourth distillation composition comprises an acid-treated stream generated from subjecting a stream comprising alkylbenzene to olefin reduction conditions including the presence of an acidic catalyst.

7. The process of claim 6 wherein the third overhead is the stream subjected to the olefin reduction conditions.

8. A process for reducing the bromine number of a stream of alkylbenzene of 15 to 25 carbon atoms containing olefinic components comprising:
   a. contacting the stream with an acidic solid under olefin reduction conditions to reduce the concentration of olefinic-components whereby benzene and heavies are produced, and an acid-treated stream is provided, and
   b. separating by distillation alkylbenzene from the acid-treated stream, said distillation providing an overhead comprising benzene, a bottoms stream comprising heavies, and a mid-cut containing alkylbenzene having less than about 1 ppm by weight benzene and less than about 50 ppm by weight heavies, said mid-cut having a bromine index of less than about 5.

9. The process of claim 8 wherein the alkylbenzene from the mid-cut has a bromine index of less than about 1.

10. An alkylbenzene refining system comprising:
   a. a benzene distillation assembly comprising an inlet adapted to receive an alkylbenzene-containing feed, an overhead outlet adapted to discharge a benzene-containing overhead stream, and a bottoms outlet adapted to discharge an alkylbenzene-containing stream;
   b a paraffins distillation assembly comprising an inlet in fluid communication with the bottoms outlet of the benzene distillation assembly, an overhead outlet adapted to discharge an alkane-containing overhead stream, and a bottoms outlet adapted to discharge an alkylbenzene-containing stream;
   c. a heavy alkylate distillation assembly comprising an inlet in fluid communication with the bottoms outlet of the paraffins distillation assembly, an overhead outlet adapted to discharge an alkylbenzene-containing overhead stream, and a bottoms outlet adapted to discharge a heavies-containing stream; and
   d. a finishing distillation assembly comprising an inlet in fluid communication with the overhead outlet of the heavy alkylate distillation assembly, an overhead outlet adapted to discharge an alkylbenzene and benzene-containing stream, a bottoms outlet adapted to discharge an alkylbenzene and heavies-containing stream, and a mid-cut outlet adapted to discharge an alkylbenzene-containing stream.

11. The apparatus of claim 10 in which the overhead outlet of the finishing distillation assembly is in fluid communication with at least one of the inlet to the benzene distillation assembly and the inlet to the paraffin distillation assembly.

12. The apparatus of claim 11 in which the bottoms outlet of the finishing distillation assembly is in fluid communication with the inlet to the heavy alkylate distillation assembly.

13. The apparatus of claim 10 in which the bottoms outlet of the finishing distillation assembly is in fluid communication with the inlet to the heavy alkylate distillation assembly.

14. The apparatus of claim 10 in which the finishing distillation assembly comprises a dividing wall column in which the inlet and mid-cut outlet are on opposite sides of the dividing wall column.

15. The apparatus of claim 10 in which the finishing distillation assembly has an internal baffle defining an internal column in fluid communication with the overhead outlet of the finishing distillation assembly and the mid-cut outlet is in fluid communication with a lower portion of the internal column.

16. The apparatus of claim 10 in which the finishing distillation assembly comprises a benzene column and a product column in which
the benzene column comprises the inlet, the overhead outlet adapted to discharge a benzene-containing stream, an overhead inlet, the bottoms outlet, and an intercolumn outlet adapted to discharge an alkylbenzene-containing stream, and
the product column comprises an inlet in fluid communication with the intercolumn outlet, an overhead outlet adapted to discharge a benzene-containing stream for return to the overhead inlet of the benzene column and a bottoms outlet adapted to discharge a purified alkylbenzene stream.

17. An alkylbenzene refining system comprising:
a. an olefin reduction catalytic converter comprising an inlet in adapted to receive an alkylbenzene-containing stream and an outlet adapted to discharge a treated, alkylbenzene-containing stream; and
b. a finishing distillation column assembly comprising an inlet in fluid communication with the outlet of the catalytic converter, an overhead outlet adapted to discharge an alkylbenzene and benzene-containing stream, a bottoms outlet adapted to discharge an alkylbenzene and heavies-containing stream, and a mid-cut outlet adapted to discharge an alkylbenzene-containing stream.

18. The apparatus of claim 17 in which the finishing distillation assembly comprises a dividing wall column in which the inlet and mid-cut outlet are on opposite sides of the dividing wall column.

19. The apparatus of claim 17 in which the finishing distillation assembly has an internal baffle defining an internal column in fluid communication with the overhead outlet of the finishing distillation assembly and the mid-cut outlet is in fluid communication with a lower portion of the internal column.

20. The apparatus of claim 17 in which the finishing distillation assembly comprises a benzene column and product column in which
the benzene column comprises the inlet, the overhead outlet adapted to discharge a benzene-containing stream, an overhead inlet, the bottoms outlet, and an intercolumn outlet adapted to discharge an alkylbenzene-containing stream, and
the product column comprises an inlet in fluid communication with the intercolumn outlet, an overhead outlet adapted to discharge a benzene-containing stream for return to the overhead inlet of the benzene column and a bottoms outlet adapted to discharge a purified alkylbenzene stream.

* * * * *